(12) United States Patent
Pandit

(10) Patent No.: US 8,328,830 B1
(45) Date of Patent: Dec. 11, 2012

(54) EAR CLEANING DEVICE

(76) Inventor: Sudhir Pandit, Hot Springs, AR (US)

( * ) Notice: Subject to any disclaimer, the term of this patent is extended or adjusted under 35 U.S.C. 154(b) by 288 days.

(21) Appl. No.: 12/857,600

(22) Filed: Aug. 17, 2010

(51) Int. Cl.
*A61M 3/02* (2006.01)
*A61F 9/00* (2006.01)
*A61F 11/00* (2006.01)

(52) U.S. Cl. .......................................... 606/162; 604/41
(58) Field of Classification Search .............. 604/39–42; 606/162
See application file for complete search history.

(56) References Cited

U.S. PATENT DOCUMENTS 5,944,711 A * 8/1999 Pender ........................... 604/514
6,485,451 B1 * 11/2002 Roberts et al. ................... 604/35

* cited by examiner

*Primary Examiner* — Kevin C Sirmons
*Assistant Examiner* — Bradley Osinski
(74) *Attorney, Agent, or Firm* — Gulf Coast Intellectual Property Group

(57) ABSTRACT

An ear cleaning device that creates a negative pressure within the patient's ear to draw fluid thereinto and provide cleansing thereof so as to substantially reduce the risk of damage to the tympanic membrane. The ear cleaning device includes a first container and a second container mechanically operably coupled together and in general axial alignment. Additionally, an ear chamber is included that is operably intermediate the first container and the second container. The ear chamber further includes a membrane to create a hermetic seal around a patient's ear. The first container is configured to receive a store a desired cleaning fluid. Operably coupled to the second container is a pressure reducing device. The ear cleaning device utilizes a hermetic seal between the second container, ear chamber and first container to transport the fluid from the first container into the ear chamber wherein the fluid is introduced in the ear canal of the patient and is subsequently collected within the second container.

17 Claims, 4 Drawing Sheets

EAR CLEANING DEVICE

FIELD OF THE INVENTION

The present invention relates to an ear cleaning device, more specifically but not by way of limitation an ear cleaning device that has a first container, a second container and an ear chamber atmospherically coupled wherein the first container has a fluid contained therein and the ear cleaning device utilizes a pressure differential between the first container and second container to transport the fluid to the ear chamber to cleanse the ear and subsequently be collected in the second container.

BACKGROUND

Healthcare practitioners routinely must clean the external ear and ear canal of patients either to prepare for a procedure or as part of a protocol for a patient during a routine visit. Typically, a fluid such as but not limited to water or alcohol is utilized to attempt to dislodge materials or wax build-up that may be present in the ear canal. Current devices that are routinely utilized by healthcare practitioners to clean the external ear and ear canal have shown to have significant limitations and design flaws that can cause damage to the patient's tympanic membrane.

One problem with current devices utilized to clean the external ear and ear canal is that the devices utilize positive pressure to inject the fluid into the ear canal. Current technology often utilized is an adapted syringe device having a plunger that is depressed to inject the fluid into the ear canal. It is assumed that the fluid injected into the ear canal will dislodge the materials and that as the fluid exits the ear canal via drainage that the materials will be included therein. This method is significantly flawed for many reasons. First, the velocity at which the fluid enters the ear canal depends upon the force applied to the plunger. This method most often results in the fluid either entering the ear canal at a velocity that is not sufficient enough to dislodge the materials or at a velocity that contains too much force thereby potentially damaging the tympanic membrane of the patient.

Additionally, the cleaning process provides no manner in which to direct or control the fluid subsequent its discharge. Typically with current conventional technology ensuing the injection of the fluid, the fluid will drain out of the ear without means to collect. Furthermore, the use of positive pressurized fluid injected into the ear canal has shown in some cases to further impact the material into the ear canal.

Accordingly, there is a need for an ear cleaning device that does not utilize positive pressure to inject fluid into the ear canal and further includes a means to capture the fluid as it exits the external ear and wherein the ear cleaning device utilizes negative pressure to accomplish the task of cleaning the ear canal.

SUMMARY OF THE INVENTION

It is the object of the present invention to provide an ear cleaning device that utilizes a combination of fluid and a negative pressure differential to clean the ear canal of a patient.

Another object of the present invention is to provide an ear cleaning device that includes a first container and a second container wherein the first container is filled with the desired cleaning fluid to be utilized to clean the ear canal of the patient.

A further object of the present invention is to provide an ear cleaning device that utilizes a second container to collect the fluid subsequent its injection into the patient's ear canal as it exits the external ear.

An additional object of the present invention is to provide an ear cleaning device that includes an ear chamber that is hermetically sealed around the exterior of the patients ear wherein the hermetic sealing of the ear chamber facilitates a negative pressurization of the ear canal of the patient.

Still another object of the present invention is to provide an ear cleaning device that includes a means to create a negative pressure differential between the first container and the second container wherein the negative pressure differential is such that the negative pressure differential draws the fluid from the first container and is introduced into the ear canal of the patient.

A further object of the present invention is to provide an ear cleaning device that includes a tube within the ear chamber having a disposable hygienic nozzle that functions to collect the fluid as exits the ear canal.

Yet a further object of the present invention is to provide an ear cleaning device that includes a suction bulb operably coupled to the second container functioning to create a negative pressure differential between the first container and the second container of the ear cleaning device.

It is a further object of the present invention to provide an ear cleaning device that is lightweight and easy to use.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
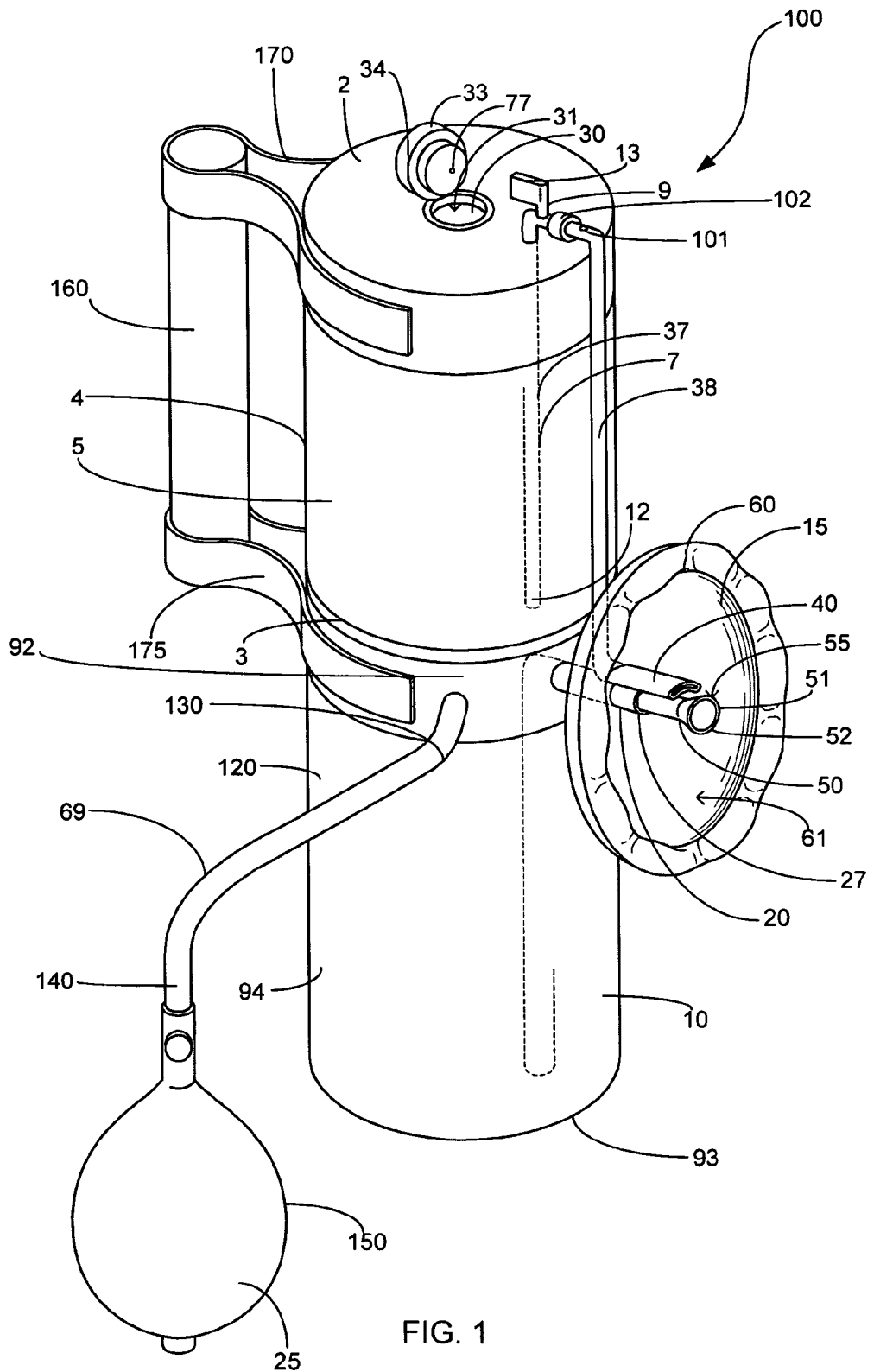
FIG. 1 is a perspective view of a preferred embodiment of the present invention.
Figure 2:
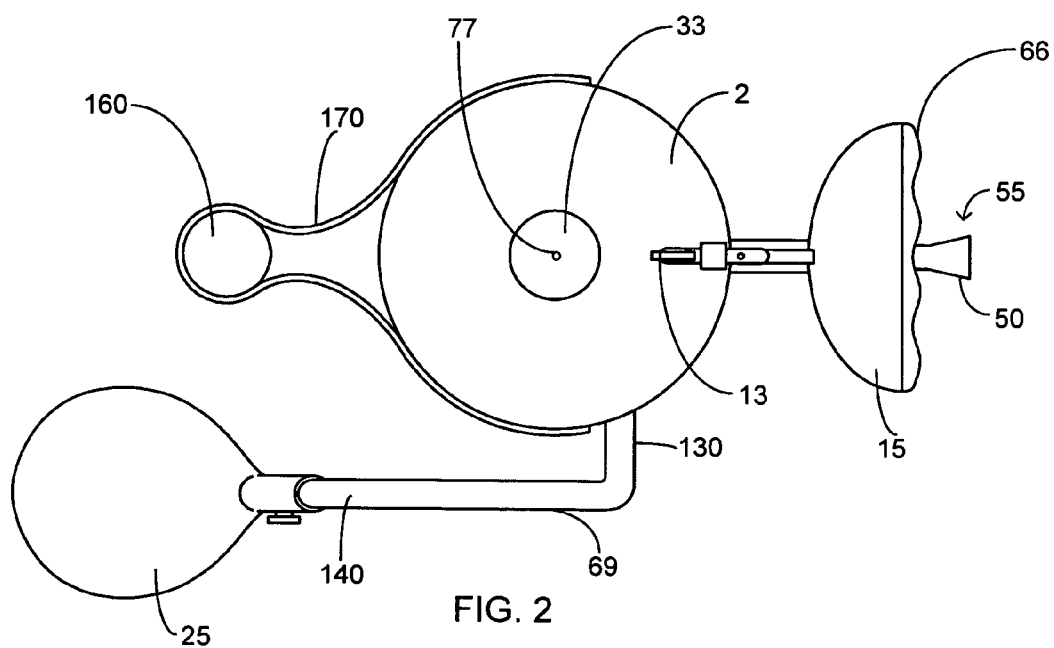
FIG. 2 is a top view of the preferred embodiment of the present invention.

Referring now to the drawings submitted herewith, wherein various elements depicted therein are not necessarily drawn to scale and wherein through the views and figures like elements are referenced with identical reference numerals, there is illustrated a ear cleaning device 100 constructed according to the principles of the present invention.

Figure 3:
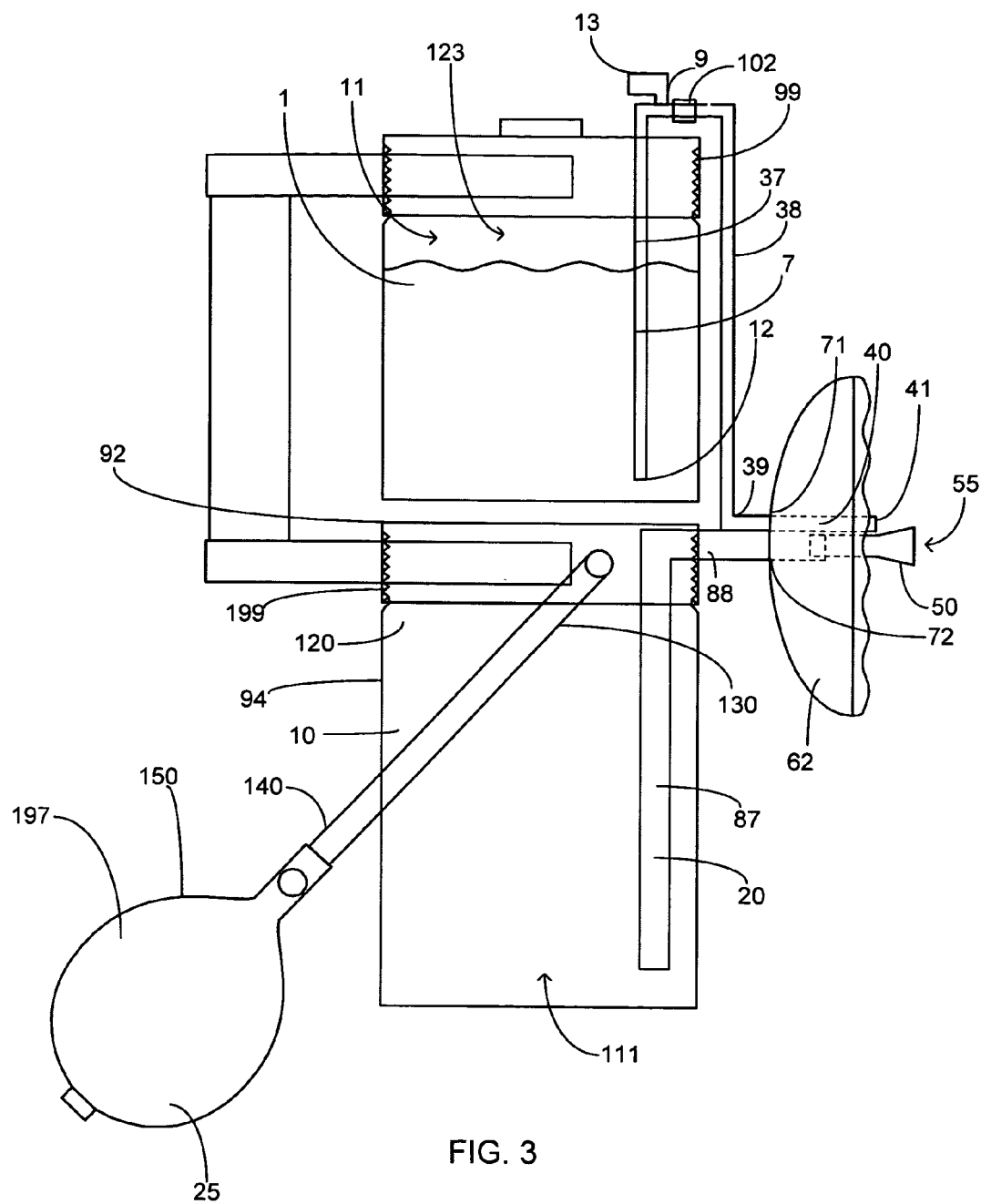
FIG. 3 is a diagrammatic side view of the preferred embodiment of the present invention.
Figure 4:
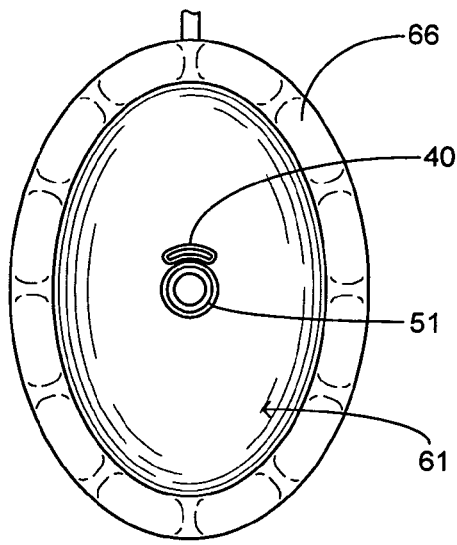
FIG. 4 is an end view of the ear cup of the preferred embodiment of the present invention.

Now referring in particular to FIGS. 1 and 3, the ear cleaning device 100 further includes a first container 5 configured to receive and retain a fluid 1 therein. The first container 5 further includes a tube 7 having a valve 9 operably engaged therewith. The tube 7 operably connects the first container 5 to an ear chamber 15. Disposed within the ear chamber 15 is a suction tube 20 functioning to operably couple the ear chamber 15 to a second container 10. A suction bulb 25 is operably engaged with the second container 10. The suction bulb 25 facilitates the reduction of pressure within the second container 10 such that the pressure within the second container 10 is lower than the pressure within the first container 5. As the first container 5 and the second container 10 are atmospherically engaged, ensuing the presence of the pressure differential between the first container 5 and the second container 10, the fluid 1 contained within the first container 5 is transferred from the first container 5 via the tube 7 to the ear chamber 15 and subsequently to the second container 10 via the suction tube 20.

The first container 5 is generally annular in shape and includes a wall 4, a bottom 3 and a top 2 formed to create an interior volume 11 configured to receive a fluid 1 therein. The first container 5 is manufactured from a suitable durable material such as but not limited to plastic or metal. The wall 4, bottom 3 and top 2 are integrally formed utilizing suitable durable methods such as but not limited to chemical or mechanical methods. While the first container 5 is illustrated herein as having one wall 4 being generally annular in shape, it is contemplated within the scope of the present invention that the first container 5 could be formed into numerous different shapes having more than one wall integrally formed to create the desired shape of the first container 5. Journaled through the top 2 is an aperture 30 that functions to supply an opening 31 so as to provide access to the interior volume 11 to facilitate the replenishment of fluid 1 as necessary. Operably engaged with the aperture 30 is a cap 33. The cap 33 further includes a seal 34 functioning to hermetically seal the cap 33 to the top 2. The seal 34 is manufactured from a suitable durable material such as but not limited to rubber. While the aperture 30 is illustrated as being centrally located on the top 2, those skilled in the art should recognize that the aperture 30 could be journaled in numerous locations on the top 2. Additionally, while the preferred embodiment of the ear cleaning device 100 includes one aperture 30 integrated into the top 2, it is additionally contemplated within the scope of the present invention that the top 2 could have more than one aperture 30 providing access to the interior volume 11. The top 2 is releasably secured to the wall 4 utilizing threads 99 shown particularly in FIG. 3. The cap 33 further includes an air hole 77. The air hole 77 is journaled through the cap utilizing suitable methods. The air hole 77 allows air to enter the portion 123 of the interior volume 11 above the fluid 1 such that the portion 123 of the interior volume 11 is maintained at a pressure that is approximately equivalent to atmospheric pressure. The atmospheric pressure of the portion 123 of the interior volume 11 acts to assist in the movement of the fluid 1 through the tube 7 when the pressure within the ear chamber 15 is lower than that of atmospheric pressure.

Disposed within the first container 5 is a tube 7. The tube 7 includes end 12 that extends into the interior volume 11 and is proximate the bottom 3. The tube 7 is manufactured from suitable durable materials such as but not limited to plastic or metal and is a conventional tube having a hollow passage to allow the fluid 1 to flow therethrough. Operably engaged with the tube 7 is the valve 9. The valve 9 functions to control the passage of fluid 1 through the tube 7. The valve 9 further functions to control the operable and atmospheric coupling of the first container 5 with the ear chamber 15 and second container 10 of the ear cleaning device 100. The valve 9 is a conventional ball valve that has a handle 13 operable to transition the valve 9 from its first position to its second position. In the second position the valve 9 is generally open thereby fluidly and atmospherically connecting the first container 5 with the ear chamber 15 and the second container 10. The tube 7 includes a first portion 37 that extends from proximate the bottom 3 of the first container 5 to the valve 9. The tube 7 further includes a second portion 38 that extends from the valve 9 exterior of the first container 5 to the elbow 39.

Journaled through the second portion 38 is a pressure release bore 101. The pressure release bore 101 is generally annular in shape and functions to restore the pressure within the tube 7 to atmospheric pressure subsequent the use of the ear cleaning device 100 thereby draining any fluid 1 retained within the tube 7. The pressure release bore 101 is hermetically sealed with the band 102. The band 102 is slidably and surroundably mounted to the second portion 38 of the tube 7. The band 102 functions to transition the pressure release bore 101 from a closed position to an open position. In the closed position the band 102 is hermetically sealed over the pressure release bore 101 allowing the atmospheric coupling of the first container 5 with the ear chamber 15 and the second container 10. Subsequent the band 102 being slidably moved away from the pressure release bore 101, the atmospheric pressure between the first container 5 and the ear chamber 15 will equalize and any fluid 1 contained within the second portion 38 of the tube 7 will be drained.

A third portion 40 of the tube 7 extends into the ear chamber 15 having an end 41 proximate the flared portion 50 of the ear nozzle 55. The third portion 40 is hermetically sealed with the ear chamber 40 using suitable durable conventional methods. The hermetic sealing of the third portion 40 of the tube 7 is required so as to atmospherically connect the ear chamber 15 with the first container 5. The third portion 40 of the tube 7 is adjacent and superposed the suction tube 20 and the ear nozzle 55. The third portion 40 of the tube 7 is formed in a semicircular manner. The shape of the third portion 40 of the tube 7 allows the fluid 1 to be discharged proximate the flared portion 50 of the ear nozzle 55 in a manner so as to allow the fluid 1 to flow over a substantial portion of the circumference the tip 51 of the ear nozzle 55. The semicircular shape of the third portion 40 of the ear nozzle 55 facilitates the entry of the fluid 1 into an ear canal of the patient more effectively than a conventional annular shaped orifice. While no particular range of degrees are required for the semicircular shape for the third portion 40 of the tube 7, good results have been achieved having a third portion 40 having a range of degree of shape that is approximately between ten degrees and two hundred and ninety degrees of the circumference of the tip 51.

Figure 5:
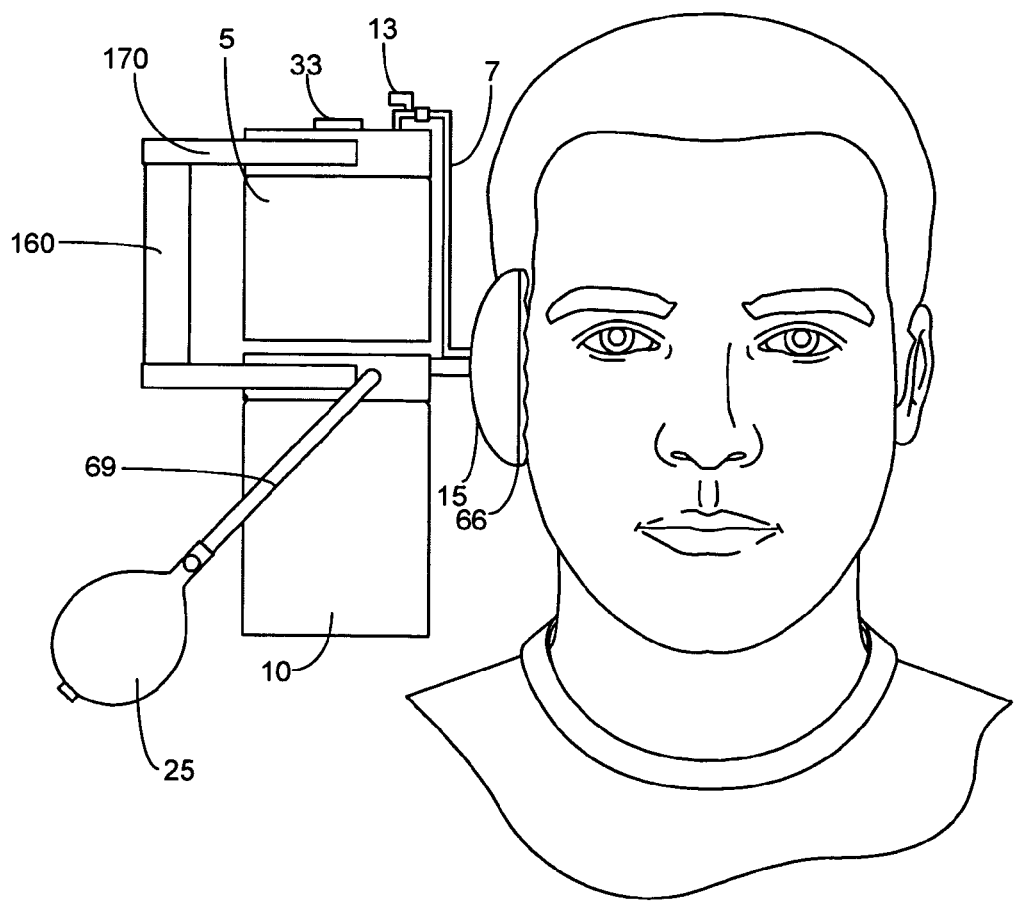
FIG. 5 is a perspective view of the preferred embodiment of the present invention engaged with a user.

The ear chamber 15 includes a generally dome shaped body 62 having a cavity 61 and further including a generally annular perimeter edge 60. The ear chamber 15 is atmospherically coupled to the first container 5 and the second container 10 via the tube 7 and suction tube 20 respectively. The unions 71, 72 for the third portion 40 and the suction tube 20 respectively, wherein the third portion 40 and suction tube 20 enter the cavity 61, are hermetically sealed utilizing conventional techniques. The unions 71, 72 are hermetically sealed so as to atmospherically couple the cavity 61 with the first container 5 and the second container 10. Circumferentially mounted proximate the perimeter edge 60 and integrally secured thereto is a membrane 66. The membrane 66 is manufactured of a suitable, durable and flexible material such as but not limited to silicone. The membrane 66 functions to create a hermetic seal around the exterior of the patient's ear as shown in FIG. 5. Those skilled in the art will recognize that numerous suitable materials could be utilized to manufacture the membrane 66. The hermetic seal created by the membrane 66 enables the atmospherical coupling of the ear chamber 15 with the first container 5 and the second container 10 thereby facilitating the flow of fluid 1 from the first container 5 to the ear chamber 15 via the tube 7 when the atmospheric pressure within ear chamber 15 and the second container 10 is less than that of the first container 5. As the fluid 1 flows through the tube 7 and into the ear chamber 15 the fluid will enter the ear canal of the patient's ear prior to exiting the suction tube 20 providing cleansing of the ear canal of the patient with little risk of damage to the tympanic membrane as no positive pressure is exerted thereon.

The suction tube 20 is a conventional tube having a hollow passage and being generally right-angled in shape having a first portion 87 and a second portion 88. The first portion 87 extends in a generally downward direction into the second container 10. The second portion 88 extends into the cavity 61 of the ear chamber 15 and is hermetically sealed therewith. A detachable ear nozzle 55 is frictionally coupled with the second portion 88 of the suction tube 20 proximate end 27. The ear nozzle 55 includes flared portion 50 and tip 51. The ear nozzle 55 has sufficient length so as to position the tip 51 of the flared portion 50 immediately adjacent the ear canal of a patient but not entering therein. A gap exists between the circumference of the tip 51 and the entrance to the patient's ear canal so as to allow the fluid 1 exiting the third portion 40 of tube 7 to flow across the tip 51 and enter the ear canal and subsequently exit through the suction tube 20 and be collected into the second container 10. It is contemplated within the scope of the present invention that the ear nozzle 55 could be manufactured in numerous different lengths so as to allow a user to select an appropriate length ear nozzle 55 in order to facilitate desired positioning of the tip 51 of ear nozzle 55 adjacent to the opening of the ear canal.

The second container 10 is in general axial alignment and coupled with the first container 5. The second container 10 is generally annular in shape and includes a wall 94, a bottom 93 and a top 92 formed to create an interior volume 111 configured to receive a fluid therein. The second container 10 is manufactured from a suitable durable material such as but not limited to plastic or metal. The wall 94, bottom 93 and top 92 are integrally formed utilizing suitable durable methods such as but not limited to chemical or mechanical methods. While the second container 10 is illustrated herein as being generally annular in shape, those skilled in the art will recognize that the second container 10 could be formed in numerous different shapes and be constructed with more than one wall 94. Additionally, while in the preferred embodiment of the present invention the second container 10 is in general axial alignment and below the first container 5, it is further contemplated within the scope of the present invention that the second container 10 could be positioned in numerous different manners with respect to the first container 5. The top 92 is releasably secured to the second container 10 proximate the upper portion 120 of the wall 94 utilizing threads 199. Those skilled in the art will recognize that the second container 10 could be releasably secured to the top 92 utilizing numerous suitable methods. The releasable securing of the top 92 functions to allow the second container 10 to be removed from the ear cleaning device 100 so as to drain the contents therein.

Integrally attached to the second container 10 is a pipe 69. The pipe 69 is generally cylindrical in shape and includes a hollow passage therein and functions to operably couple the suction bulb 25 to the second container 10. The suction bulb 25 is a conventional collapsible suction bulb having a cavity 197 and a wall 150 that is manufactured from a durable resilient material such as but not limited to rubber. The user depresses the wall 150 to transition the suction bulb 25 from its first position to its second position and subsequently releases the suction bulb 25 such that the suction bulb 25 commences to draw a vacuum within the second container 10. The pipe 69 is hermetically sealed at end 130 to the second container 10 and at end 140 to the suction bulb 25. The hermetic seal of the pipe 69 allows the user to engage the suction bulb 25 and reduce the atmospheric pressure of the interior volume 111 of the second container 10 to a pressure that is lower than that of atmospheric pressure. As the user engages the suction bulb 25 and manipulates the suction bulb 25 between its first and second position, the atmospherically coupled first container 5 will begin to equalize with the second container 10. With the valve 9 in its open position and the membrane 66 hermetically sealed circumferentially around the exterior of a patient's ear, the atmospheric imbalance between the second container 10 and the first container 5 creates a negative pressure within the ear chamber 15. Natural equilibration principles will move the fluid 1 from the first container 5 into the ear chamber 15 via tube 7 and subsequently into the ear canal of the patient. The fluid 1 continues to move through the suction tube 20 until the pressure within the ear cleaning device 100 is equalized intermediate the second container 10 and the first container 5. As the fluid 1 is drawn into the ear canal, the fluid 1 functions to dislodge any debris and provide general cleaning of the ear canal prior to exiting via the suction tube 20.

An arm 160 is coupled to the first container 5 and second container 10. The arm 160 is generally cylindrical in shape and functions as an interface for a user to grasp the ear cleaning device 100. The arm 160 is manufactured from a suitable durable material such as but not limited to plastic or metal. The arm 160 is generally cylindrical in shape but it is contemplated within the scope of the present invention that the arm 160 could be formed in numerous different shapes and still achieve the desired function as described herein. The arm 160 has coupled thereto an upper member 170 and a lower member 175. The upper member 170 and the lower member 175 are secured to the arm 160 using suitable chemical and/or mechanical methods. The upper member 170 and lower member 175 are mounted to the arm 160 in a generally perpendicular manner. The upper member 170 is surroundably mounted to a portion of the top 2 and is secured thereto utilizing suitable chemical or mechanical methods. The lower member 175 extends perpendicularly from the arm 160 and is surroundably mounted to a portion of the top 92 of the second container 10.

A description of the operation of the ear cleaning device 100 is as follows. In use, the user will at least partially fill the interior volume 11 of the first container 5 with a desirable cleaning fluid 1 via the aperture 30. The aperture 30 is hermetically sealed with the cap 33. Ensuing the filling of the fluid 1 into the first container 5, the user will place the ear chamber 15 proximate a patient's ear such that the membrane 66 will circumferentially surround the exterior of the patient's ear. The user applies a force in the general direction of the patient to enable a hermetic seal to be formed around the ear. The user ensures that the band 102 is positioned over the pressure release bore 101 and that the valve 9 is in s substantially open position. Following placement of the ear chamber 15, the user will begin to manipulate the suction bulb 25 between its first and second position. As the user manipulates the suction bulb 25 between its first and second position the atmospheric pressure within the second container 10 is reduced. As the second container 10 is atmospherically coupled to the ear chamber 15 the negative pressure within the ear chamber 15 begins to draw the fluid 1 into the tube 7. The fluid 1 is drawn into the second portion 38 of the tube 7 and then the third portion 40 of the tube as a sufficient negative pressure differential is created through manipulation of the suction bulb 25. The fluid 1 exits the third portion 40 of the tube and enters the ear canal wherein the fluid is subsequently drawn into the suction tube 20 by the negative pressure differential of the second container 10. The fluid 1 exits the suction tube 20 and is collected in the second container 10. The user continues to manipulate the suction bulb 25 to maintain the negative pressure differential within the second container 10 wherein the pressure differential acts to draw the fluid 1 from the first container 5 into the tube 7, propagating into the patient's ear canal and subsequently drawn into the suction tube 20 where the fluid 1 is collected in the second container 10. The user continues this process until the desired cleaning of the ear canal is accomplished. Upon completion of the ear canal cleansing, the user will transition the valve 13 to its closed position and engage the band 102 to slidably traverse the band 102 across the tube 7 so as to place the pressure release bore 101 in a substantially open position. As the first container 5 is now operably disconnected, the fluid 1 remaining in the tube 7 will travel through the tube 7 and into the ear canal of the patient, wherein the fluid 1 egresses through the suction tube 20 as a result of the negative pressure differential existing in the second container 10. Ensuing the fluid 1 having been evacuated from the tube 7, ear canal and suction tube 20 the pressure within the ear chamber 15 and the second container 10 will equalize to that of approximately atmospheric pressure as the hermetic seal of the pressure release bore 101 has been disengaged. This ensures that substantially all of the fluid 1 has been evacuated through the tube 7 and suction tube 20 and deposited into the second container 10 thereby eliminating any spillage of fluid 1 onto the patient upon removal of the ear cleaning device 100.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. An ear cleaning device comprising:
   a first container, said first container having at least one wall, a bottom and a top configured to define an interior volume for receiving a fluid therein;
   a second container, said second container operably coupled to said first container, said second container having at least one wall, a bottom, and a top configured to define an interior volume, said second container operable to receive the fluid from said first container, said second container being hermetically sealed to said first container;
   an ear chamber, said ear chamber being operably intermediate said first container and said second container, said ear chamber configured to be hermetically sealed against a patient's ear;
   a valve, said valve operable to control the flow of fluid from said first container into said ear chamber, said flow of fluid induced by the atmospherical pressure within said ear chamber being lower than that of said first container;
   a membrane, said membrane configured to encircle a patient's ear and be hermetically sealed thereto; and
   wherein said second container is operable to have the atmospheric pressure reduced therein so as to facilitate the negative pressurization of the ear cleaning device such that the negative pressurization is operable to draw the fluid from said first container into said ear chamber and cleanse the ear canal of the patient.

2. The ear cleaning device as recited in claim 1, and further including a suction bulb, said suction bulb operably connected to said second container said suction bulb functioning to reduce the pressure within said second container to a pressure that is lower than the atmospheric pressure.

3. The ear cleaning device as recited in claim 2, and further including a fluid tube, said fluid tube configured to transport fluid from said first container to said ear chamber, wherein the fluid is transported to said ear chamber using a negative pressure differential between said ear chamber and said first container.

4. The ear cleaning device recited in claim 3, and further including a suction tube, said suction tube operable to transport fluid from said ear chamber to said second container.

5. An ear cleaning device operable to produce a pressure that is below that of atmospheric pressure within a patient's ear to provide cleansing thereof comprising;
   a first container, said first container having one wall, a bottom and a top configured to define an interior volume, said first container being generally annular in shape;
   an ear chamber, said ear chamber being generally annular and dome shaped having a cavity configured to engage a human ear, said ear chamber operably connected to said first container, said ear chamber and said first container being hermetically sealed to each other, said ear chamber further configured to hermetically seal against a human ear;
   a second container, said second container having one wall, a bottom and a top configured to define an interior volume, said interior volume operable to receive a fluid therein, said second container being hermetically sealed to said ear chamber, said second container configured to be proximate and coupled to said first container;
   a pressure reducing device, said pressure reducing device operably coupled to said second container, said pressure reducing device configured to reduce the atmospheric pressure within said second container; and
   wherein upon said second container having a pressure that is lower than that of the atmospheric pressure, the fluid disposed within said first container will be transported into said ear chamber as a result of the negative pressurization induced by said pressure reducing device and be introduced into the human ear wherein the fluid is subsequently transported into said second container for collection.

6. The ear cleaning device as recited in claim 5, and further including a membrane, said membrane circumferentially mounted to said ear chamber, said membrane operable to provide a hermetic seal around a patient's ear so as to atmospherically couple said ear chamber to said second container.

7. The ear cleaning device as recited in claim 6, and further including a fluid tube, said fluid tube having a first end and a second end, said first end of said fluid tube proximate said bottom of said first container, said second end of said fluid tube being located within a said cavity of said ear chamber, said fluid tube operable to transport the fluid disposed within said first container into said ear chamber upon the ear chamber having a pressure therein that is lower than that of the first container.

8. The ear cleaning device as recited in claim 7, wherein said second end of said fluid tube is semi-circular in shape, said second end facilitating the introduction of the fluid into the ear canal of the human ear.

9. The ear cleaning device as recited in claim 8, and further including a suction tube, said suction tube having a first end and a second end, said first end of said suction tube being disposed within said cavity of said ear chamber, said second end of said suction tube being proximate said bottom of said second container, said suction tube operable to transport the fluid from the ear canal of the human ear engaged with the ear cleaning device to said second container.

10. The ear cleaning device as recited in claim 9, and further including an ear nozzle, said ear nozzle releasably secured to said first end of said suction tube, said ear nozzle having a first end and a second end, said second end of the said ear nozzle being adjacent the opening of the ear canal of the human ear engaged with the ear cleaning device.

11. The ear cleaning device as recited in claim 10, and further including a valve, said valve operable to control the flow of fluid from said first container into said ear chamber, said valve having a first position and a second position, said flow of fluid induced by the atmospherical pressure within said ear chamber being lower than that of said first container.

12. An ear cleaning device operable to utilize a negative pressure within a patient's ear so as to substantially avoid damage to the tympanic membrane during cleansing thereof comprising;
   a first container, said first container having one wall, a bottom and a top configured to define an interior volume, said top being releasably secured to said one wall, said first container being generally annular in shape, said first, container further including an aperture, said aperture being present in said top, said aperture configured to allow fluid to be poured therethrough, said first container further including a tube, said tube having a first end and a second end, said tube configured to transport a fluid;
   an ear chamber, said ear chamber being generally annular and dome shaped having a cavity configured to engage a human ear, said ear chamber operably connected to said first container, said ear chamber and said first container being hermetically sealed to each other, said second end of said tube being located within said ear chamber, said ear chamber further configured to hermetically seal against a human ear;
   a second container, said second container having one wall, a bottom and a top configured to define an interior volume, said top being releasably secured to said wall, said interior volume operable to receive a fluid therein, said second container being operably coupled to said ear chamber, said second container being hermetically sealed to said ear chamber, said second container configured to be proximate and coupled to said first container;
   a pressure reducing device, said pressure reducing device operably coupled to said second container, said pressure reducing device configured to reduce the atmospheric pressure within said second container;
   a valve, said valve operably connected to said tube, said valve operable to control the flow of fluid from said first container into said ear chamber, said valve having a first position and a second position, said flow of fluid induced by the atmospherical pressure within said ear chamber being lower than that of said first container; and
   wherein upon said second container having a pressure that is lower than that of atmospheric pressure, the fluid disposed within said first container will be transported into said ear chamber as a result of the negative pressurization induced by said pressure reducing device and be introduced into the human ear wherein the fluid will cleanse the ear canal of the human ear and subsequently be transported into said second container for collection.

13. The ear cleaning device as recited in claim 12, and further including a suction tube, said suction tube having a first end and a second end, said first end of said suction tube being disposed within said cavity of said ear chamber, said second end of said suction tube being proximate said bottom of said second container, said suction tube operable to transport the fluid from the ear canal of the human ear engaged with the ear cleaning device to said second container.

14. The ear cleaning device as recited in claim 13, and further including an ear nozzle, said ear nozzle having a first end and a second end, said second end of said ear nozzle being flared in shape, said first end of said ear nozzle releasably secured to said first end of said suction tube, said second end of said ear nozzle being adjacent the opening of the ear canal of the human ear engaged with the ear cleaning device.

15. The ear cleaning device as recited in claim 14, wherein said second end of said tube is semi-circular in shape, said second end of said tube facilitating the introduction of the fluid into the ear canal of the human ear.

16. The ear cleaning device as recited in claim 15, wherein said first container and said second container are mechanically coupled, said first container and said second container being in general axial alignment, said second container being underneath said first container.

17. The ear cleaning device as recited in claim 16, wherein said pressure reducing device is a suction bulb.

* * * * *